US009046473B2

(12) United States Patent
Levine et al.

(10) Patent No.: US 9,046,473 B2
(45) Date of Patent: Jun. 2, 2015

(54) METHOD AND APPARATUS FOR DETECTING THE PRESENCE OF INTRAERYTHROCYTIC PARASITES

(71) Applicants: Robert A. Levine, Guilford, CT (US); Michael B. Jorgensen, New Haven, CT (US)

(72) Inventors: Robert A. Levine, Guilford, CT (US); Michael B. Jorgensen, New Haven, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

(21) Appl. No.: 13/630,934

(22) Filed: Sep. 28, 2012

(65) Prior Publication Data
US 2013/0078668 A1 Mar. 28, 2013

Related U.S. Application Data (60) Provisional application No. 61/540,310, filed on Sep. 28, 2011, provisional application No. 61/635,065, filed on May 11, 2012.

(51) Int. Cl.
*C12Q 1/04* (2006.01)
*G01N 21/21* (2006.01)
*G01N 21/64* (2006.01)
*G01N 33/72* (2006.01)
*G01N 33/80* (2006.01)

(52) U.S. Cl.
CPC ............ *G01N 21/21* (2013.01); *G01N 21/6458* (2013.01); *G01N 33/721* (2013.01); *G01N 33/80* (2013.01); *G01N 2333/43526* (2013.01); *G01N 2333/44* (2013.01); *G01N 2800/107* (2013.01)

(58) Field of Classification Search
USPC .................................................... 435/34, 29
See application file for complete search history.

(56) References Cited

U.S. PATENT DOCUMENTS

| 2003/0151735 A1 | 8/2003 | Blumenfeld et al. |
| 2009/0238437 A1 | 9/2009 | Levine et al. |
| 2009/0253218 A1 | 10/2009 | Wardlaw et al. |
| 2011/0059481 A1* | 3/2011 | Wardlaw et al. ............. 435/29 |
| 2011/0204257 A1 | 8/2011 | Wiseman et al. |

OTHER PUBLICATIONS

Esposito et al., FRET imaging of hemoglobin concentration in *Plasmodium falciparum*-infected red cells. PLoS One, vol. 3 No. 11 (Nov. 21, 2008) pp. 1-10.*
Corbett et al., Effect of hemoglobin concentration on nucleation and polymer formation in sickle red blood cells. The Journal of Biological Chemistry, vol. 270, No. 6 (Feb. 10, 1995) pp. 2708-2715.doi: 10.1074/jbc.270.6.2708.*

(Continued)

*Primary Examiner* — Jon P Weber
*Assistant Examiner* — Kara Johnson
(74) *Attorney, Agent, or Firm* — O'Shea Getz P.C.

(57) ABSTRACT

An apparatus and method for determining the presence of an intraerythrocytic organism within a sample of liquid whole blood is provided. The method includes the steps of a) creating an image of the sample quiescently residing within a sample chamber; b) evaluating the image for the presence of at least one red blood cell within the image containing at least one first region of decreased hemoglobin content and/or hemoglobin concentration within the red blood cell, which red blood cell has an otherwise homogenous distribution of hemoglobin; and c) determining the presence of an intraerythrocytic organism within the sample using the evaluation of the image.

14 Claims, 8 Drawing Sheets

(56) References Cited

OTHER PUBLICATIONS

Esposito et al., Quantitative imaging of human red blood cells infected with *Plasmodium falciparum*. Biophysical Journal, vol. 99 (Aug. 2010) pp. 953-960.*

Sensitivity of Hemozoin Detection by Automated Flow Cytometry in Non- and Semi-Immune Malaria Patients Grobusch et al. Cytometry Part B (Clynical Cytometry) 55B: 46-51 (2003).

Clearance Kinetics of Parasites and Pigment-Containing Leukocytes in Severe Malaria Day et al. bloodjournal, hematologylibrary 1996 88: 4694-4700.

Detection of Imported Malaria With the Cell-DYN 4000 Hematology Analyzer Weyer et al. Journal of Clinical Microbiology Dec. 2002, p. 4729-4731.

Diagnosis of Malaria by Magnetic Deposition Microscopy Zimmerman et al. Am. J. Top. Med. Hyg., 74(4) 2006, pp. 568-572.

Evaluation of the Abbott Cell-DYN 4000 Hematology Analyzer for Detection and Therapeutic Monitoring of *Plasmodium vivax* in the Republic of Korea Suh et al. Tropical Medicine and International Health vol. 8 No. 12 pp. 1074-1081 Dec. 2003.

Automated Detection of Malaria Pigment in White Blood Cells for the Diagnosis of Malaria in Portugal Hansheid et al. Am. J. Trop. Med. Hyg., 64 (5, 6) 2001, pp. 290-292.

Automated Detection of Malaria-Associated Intraleucocytic Haemozoin by Cell-DYN CD4000 Depolarization Analysis Scott et al. Clin. Lab. Haem. 2003, 24, 77-86.

Malaria Diagnosis With the Haematology Analyser Cell-DYN 3500(tm): What Does the Instrument Detect Hanscheid et al. Clin. Lab. Haem. 2000, 22, 259-261.

Intraleucocytic Malaria Pigment and Prognosis in Severe Malaria Phu et al. Transactions of the Royal Society of Tropical Medicine and Hygiene (1995) 89, 200-204.

Is It Cerebral Malaria.? J.O.O. Commey Centre for Tropical Clinical Pharmacology and Therapeutics, Department of Child Health, University of Ghana Medical School, Accra, Ghana, Lancet. Nov. 3, 1984 (8410 ) :1037.

Automated Malaria Detection by Depolarization of Laser Light Mendelow et al. British Journal of Haematology 1999, 104, 499-503.

Intraleucocytic Malaria Pigment and Clinical Severity of Malaria in Children Amodu et al. Transactions of the Royal Society of Tropical Medicine and Hygiene (1998) 92, 54-56.

Hemoglobin Catabolism and Iron Utilization by Malaria Parasites Rosenthal et al. Molecular and Biochemical Parasitology 83 (1996) 131-139.

Huy et al. "A Simple and Rapid Colorimetric Method to Measure Hemozoin Crystal Growth in Vitro", Analytical Biochemistry, vol. 354, No. 2, Jul. 15, 2006, pp. 305-307.

Oliveria et al. "Structural and Morphological Characterization of Hemozoin Produced by Schistosoma Mansoni and Thodnius Prolixus", Febs Letters, vol. 579, No. 27, Nov. 7, 2005, pp. 6010-6016.

Vink et al., "An automatic vision-based malaria diagnosis system", Journal of Microscopy, vol. 250, Issue 3, 2013, pp. 166-178.

\* cited by examiner

METHOD AND APPARATUS FOR DETECTING THE PRESENCE OF INTRAERYTHROCYTIC PARASITES

The present application is entitled to the benefit of and incorporates by reference essential subject matter disclosed U.S. Provisional Application No. 61/540,310 filed Sep. 28, 2011 and U.S. Provisional Application No. 61/635,065 filed May 11, 2012.

BACKGROUND OF THE INVENTION

1. Technical Field

The present invention relates to apparatus and methods for analysis of biologic fluid samples (e.g., blood) in general, and for the detection of anisotropic crystals within the samples in particular.

2. Background Information

Anisotropic (also referred to as birefringent) crystals are not usually present in liquid whole blood of healthy subjects. Whole blood that is allowed to dry will generally result in the precipitation/formation of crystals and particles that are anisotropic but have no readily detectable anisotropic features while they are in solution. Anisotropic solid substances that may be present in un-dried whole blood include: 1) phagocytosed uric acid crystals (seen in acute gout), 2) phagocytosed cholesterol crystals seen in degenerative states of intra-arterial plaque in which plaque is phagocytosed, 3) phagocytosed Charcot-Leyden crystals found in degenerating eosinophils, and 4) hemozoin, a waste product of hemoglobin digestion by hematophagous parasites infecting the vertebrate host such as those in the order Haemosporida. Other parasites that ingest hemoglobin and excrete hemozoin include Schistosomes, an important cause of morbidity throughout the world. Perhaps the medically most important cause of the presence of circulating anisotropic crystals in whole blood in humans is infection with malaria in which the crystals are hemozoin and seen in a small proportion of the red blood cells and in some cases in some monocytes and neutrophils, although the detection and identification of the other mentioned crystals is also potentially clinically useful. Hemozoin is a waste product of the parasites digestion of the red cell's hemoglobin. Red blood cells infected with malarial parasites will have significant decreases in their hemoglobin content and or concentration due to the ingestion of the hemoglobin by the parasite and its eventual excretion as the waste product, hemozoin. The formation of crystalline of hemozoin renders it non-toxic to the parasite. *Babesia* are another genus, with over 100 species, of protozoa that are clinically important members of the order Haemosporida. Both malaria and *Babesia* are found in many species of vertebrates in addition to humans. Birds and reptiles are common hosts. *Babesia*, in contrast to similar appearing malarial protozoans, according to the literature, do not have hemozoin associated with their infection. This absence of hemozoin in *Babesia* infections can be of utility in distinguishing the morphologically similar *Babesia* forms from malarial infections, but obviously hemozoin detection cannot be used as a screening tool for the detection of *Babesia* infection. *Haemoproteus* is another genus of protozoa that are parasitic in birds, reptiles and amphibians. These protozoa infect both wild birds and birds in the food chain such as turkeys. The protozoa, like malaria, produce hemozoin.

Hemozoin may be found both in the red blood cells that are infected with the hematophagous parasites or in neutrophils or monocytes that have phagocytosed the infected red blood cells containing the hemozoin or have phagocytosed the free hemozoin released by lysed red blood cells or excreted by the parasite.

While the detection of hemozoin has been used to alert the physician to the possibility of the host organism being infected with a hemozoin excreting parasite, the utility of looking for hemozoin is presently severely limited by the complexity of the methods employed to detect it. Current techniques to discover the hemozoin in erythrocytes or white blood cells from patients with malaria require a relatively high-powered microscope and often require the use of dark field or polarized microscopy. Such instruments are expensive and not suitable for field use.

SUMMARY OF THE INVENTION

According to a first aspect of the present invention, a method for detecting the presence of anisotropic crystals within a biologic fluid sample is provided. The method includes the steps of: a) disposing the sample within a sample chamber in a sample layer having a height not greater than about fifteen microns (15μ); b) disposing the sample layer within the sample chamber between a polarizing filter having a polar orientation and an analyzing filter having a polar orientation; c) disposing the polarizing filter, sample chamber, and analyzing filter in a configuration relative to a light source such that light from the light source passes through the polarizing filter and becomes polarized light, and the polarizing light subsequently passes through the sample, and subsequently impinges on the analyzing filter; and d) wherein the polar orientations of the polarizing filter and the analyzing filter are such that the polarized light will not pass through the analyzing filter, and light passing through an anisotropic crystal disposed within the sample will pass through the analyzing filter and appear as a point of light. The light passing through the anisotropic crystal is able to pass through the analyzing filter because its polar orientation changes as it passes through the anisotropic crystal prior to encountering the analyzing filter. The light passing through the analyzing filter appears as a point of light.

According to another aspect of the present invention, an apparatus for detecting the presence of anisotropic crystals within a biologic fluid sample is provided. The apparatus includes a housing, a sample chamber, a polarizing filter, an analyzing filter, and a light source. The sample chamber has a chamber height not greater than about fifteen microns (15μ), and the chamber is selectively disposable within the housing. The polarizing filter has a polar orientation, and is disposable within the housing on a first side of the sample chamber. The analyzing filter has a polar orientation, and is selectively disposable within the housing on a second side of the sample chamber, opposite the first side. The light source is positioned such that light from the light source passes through the polarizing filter and becomes polarized light, and the polarizing light subsequently passes through the sample disposed within the chamber, and subsequently impinges on the analyzing filter. In a first configuration the polar orientations of the polarizing filter and the analyzing filter are crossed, and the polarized light will not pass through the analyzing filter. Light passing through an anisotropic crystal disposed within the sample will have a modified polar orientation and will pass through the analyzing filter in the first configuration.

According to another aspect of the present invention, a biologic fluid sample chamber is provided that includes a base plate, an upper panel, at least three separators, and at least one of a positive control area and a negative control area disposed within the chamber between the base plate and an upper panel. The base plate and the upper panel comprise a transparent and isotropic material. The at least three separators are disposed between the base plate and the upper panel. The positive control area contains anisotropic elements and the negative control area does not contain anisotropic elements.

According to another aspect of the present invention, a method for detecting the presence of hemozoin crystals within a red blood cell in a biologic fluid sample is provided. The method includes the steps of: a) disposing the sample within a sample chamber in a sample layer having a height not greater than about fifteen microns (15μ); b) imaging the sample by transmitting light through the sample at a wavelength in the range of about 410-420 nm, and identifying red blood cells within the image; and c) evaluating the red blood cells for the presence of at least one area of low transmission, which area of low transmission is indicative of the presence of a hemozoin crystal within the red blood cell.

According to another aspect of the present invention, a method of determining the presence of an intraerythrocytic organism within a sample of liquid whole blood is provided. The method includes the steps of a) creating an image of the sample quiescently residing within a sample chamber; b) evaluating the image for the presence of at least one red blood cell within the image containing at least one first region of decreased hemoglobin content and/or hemoglobin concentration within the red blood cell, which red blood cell has an otherwise homogenous distribution of hemoglobin; and c) determining the presence of an intraerythrocytic organism within the sample using the evaluation of the image.

According to another aspect of the present invention, an apparatus for determining the presence of an intraerythrocytic organism within a sample of liquid is provided. The apparatus includes a sample chamber, one or more light sources, one or more light detectors, and a programmable analyzer. The sample chamber is operable to quiescently hold the sample. The light source is operable to selectively transmit light through the sample chamber. The light detector is operable to detect light transmitted through the sample chamber and produce representative light signals. The programmable analyzer is adapted to receive the light signals, produce an image of the sample quiescently residing within the chamber, evaluate the image for the presence of at least one red blood cell within the image containing at least one first region of decreased hemoglobin content and/or hemoglobin concentration within the red blood cell, which red blood cell has an otherwise homogenous distribution of hemoglobin, and determine the presence of an intraerythrocytic organism within the sample using the evaluation of the image.

The present invention examines a layer of biologic fluid sample for the presence of anisotropic crystals using cross polarization of light passing through the sample. Incident light is passed through a polarizing filter where it is polarized, subsequently passed through the specimen, and is subsequently subjected to an analyzing filter. The polarity orientation of the analyzing filter can be oriented to not allow the polarized light (from the first filter) to pass through the analyzing filter. If the polarized light passing through the sample interacts with an anisotropic crystal, however, the polarity of the light passing through the crystals will change and will thereafter pass through the analyzing filter, becoming detectable against the dark background created by the polarized analyzing filter. Hence, the presence of anisotropic crystals may be detected.

In some embodiments, one or both of the polarizing filter and analyzing filter are selectively movable (e.g., rotatable) relative to the other to a non cross-polar orientation (i.e., an "open" orientation) where the polar axis of each filter is aligned. In a configuration wherein both the polarizing filter and the analyzing filter have the same polarity orientation, light can be transmitted through both filters 32, 34, where after it can be detected and analyzed. In an analysis mode, epi-fluorescent light can be passed through one of the filters, or one or both of the filters can be moved out of the light path instead of rotating one so that their polarity is uncrossed. When the insertion or removal of the polars from the light path is employed, they can be oriented in the crossed position when present in the light path.

The present method permits the examination of whole blood or other biologic fluids for the presence of hemozoin as well as other anisotropic crystals without significant dilution. If such crystals are found, a more detailed examination of the patient's blood or biological fluids can be performed to determine the nature and location and size of the crystals. In particular, the detailed examination may be facilitated by examining the liquid blood which has been suitably stained with a supravital stain (e.g., acridine orange) and examined with fluorescent microscopy for the presence of malarial parasites at the exact location of the detected hemozoin within the red cell containing the hemozoin. The detailed examination of those red blood cells shown to contain hemozoin may be subsequently be performed. U.S. Pat. Nos. 7,951,599; 7,929,122; and 7,903,241, and U.S. Patent Application Ser. No. 61/371,020, all of which are hereby incorporated by reference in their entirety, describe a reader and apparatus operable to determine hemoglobin content of individual red blood cells, as well as absorption of transmitted light at chosen wavelengths and fluorescent emissions from the sample for purposes of additional analyses on the sample.

Whole blood is composed of many compounds that, when crystallized, will depolarize light. However, these compounds have no impact with respect to affecting the polarization of transmitted light while they are in solution, unless the path length is sufficiently large (centimeters). Glucose (dextrose) is an example of such a compound. Additionally, whole blood is also quite opaque unless it is in a thin layer; i.e., nearly a monolayer in thickness. Light that passes through a sample of whole blood disposed in a layer greater than fifteen microns (15μ) is greatly scattered. In view of that light scattering, it is preferable to evaluate an undiluted whole blood sample disposed in a layer having a thickness on the order of equal to or less than fifteen microns; 15μ. Hemozoin can be efficiently detected within a liquid whole blood sample by examining the aforesaid thin layer (preferably only one to several cells thick) of the sample for the presence of anisotropic crystals. The thin layer prevents red blood cells not containing hemozoin from obscuring the transmission of light through the anisotropic crystals.

A chamber in which a sample of undiluted, whole liquid blood is disposed in a thin layer where cells are relatively immobile (e.g., a monolayer) is particularly desirable. In such a chamber, the visible light signal created by light passing through one or more anisotropic crystals, and their location within the chamber (or relative to one other) will not be extinguished or greatly diminished by superimposed relatively opaque red blood cells. In fact, the location of the light signal can be used to determine if the crystal is extracellular or intracellular, and if it is intracellular, the cell type, etc. Preferably, the chamber is configured to impede evaporation of blood within the chamber for at least a minute or two (1-2) after the sample is disposed within the chamber, and the chamber is preferably free of any anisotropy.

Such a chamber could be filled with a small amount of blood (100 to 500 nanoliters), examined under field conditions and/or in a laboratory by a magnifier in combination with a light source, a polarizing filter, and an analyzing filter (e.g., an opaque tube with non reflective interior surfaces, free of significant light leaks, holding the chamber, a polarizing filter, and an analyzing filter). The light source could be daylight (if sufficiently bright) or an electrically-powered light source. The presence of light points in the specimen when examined through the filters 32, 34 in a cross polarized configuration would indicate the presence of anisotropic crystals present in the sample. For some analyses, a positive determination of the existence of anisotropic crystals within the sample may be adequate information for treatment purposes (e.g., in areas where there is a high incidence rate of malaria). In other instances, a sample that proves positive for anisotropic crystals in the initial screening step can then be examined further to provide useful clinical information.

Potential uses for the present invention include: a) screening for malaria infection; b) discriminating *Babesia* infections from malarial infections; c) screening for acute myocardial infarction and or stroke or other vascular events due to ruptured plaque; d) screening for any parasite that produces hemozoin; e) screening for acute gout in cases of an acute arthritis; 1) quantifying the degree of malaria or *Babesia* infection in a patient's blood (i.e. automatic calculation of parasitemia magnitude); g) speciation of malarial infections based on size and or shape and or location of hemozoin; h) screening for Shistosomiasis; i) screening for bet-amyloid protein (BAP), associated with Alzheimer disease in peripheral blood or cerebral spinal fluid (CSF), and wherein Congo red dye may be added to the specimen to make the BAP anisotropic; and j) detection of Haemoproteus infections in birds, reptiles and amphibians.

The present method and advantages associated therewith will become more readily apparent in view of the detailed description provided below, including the accompanying drawings.

BRIEF DESCRIPTION OF THE DRAWINGS

The application file contains at least one drawing executed in color. Copies of this patent or patent application publication with color drawing(s) will be provided by the Office upon request and payment of the necessary fee.

DETAILED DESCRIPTION OF EMBODIMENTS OF THE INVENTION

According to an aspect of the present invention, a method and apparatus for screening a biological fluid sample (e.g., undiluted whole blood) for the presence of anisotropic crystals is provided. According to another aspect of the present invention, a method and apparatus for screening and analyzing a biological fluid sample containing anisotropic crystals is provided.

Referring to FIGS. 1-4, the present invention utilizes a sample chamber 10 that includes a base plate 12 and an upper panel 14, both of which are transparent and comprised of an isotropic material. Cyclic polyolefin (e.g., Zeonex® offered by Nippon Zeon Co. Ltd., of Tokyo Japan) is an example of an acceptable material, but the chamber 10 is not limited to this particular material. Glass can also be used as an isotropic material, but lacks an amount of flexibility that facilitates the creation of a sample chamber of uniform height, as is described in U.S. Patent Publication No. 2007/0243117 and U.S. patent application Ser. No. 12/971,860, both of which are hereby incorporated by reference in its entirety. Using an isotropic material for the base plate 12 and upper panel 14 (and separators 24 described below) is preferable to prevent optical rotation of light passing there through. A further advantage to using a chamber formed using a flexible material as described in the aforesaid Publication and application is that it facilitates further analysis of a hematological sample; e.g., permitting the determination of valuable hematological data as well as the determination of the presence of malaria. The sample chamber 10 is formed between the opposing surfaces 16, 18 of the base plate 12 and upper panel 14 (i.e., the "interior surfaces"), respectively. Within the sample chamber 10, the interior surfaces 16, 18 of the base plate 12 and the upper panel 14 are spaced apart from one another and are configured to receive a fluid sample there between for image analysis. The distance between the opposing interior surfaces of the two panels (i.e., "chamber height 20") is such that a biologic fluid sample disposed between the two surfaces 16, 18 will contact both surfaces.

In some embodiments, the sample chamber 10 is further defined by lateral boundaries 22 that contain the lateral spread of the sample within the chamber 10; e.g., a lateral boundary 22 may be formed by a hydrophobic coating applied to one or both interior surfaces 16, 18, or by a bead of adhesive (or other formable) material extending between the interior surfaces, or by a physical configuration that stops lateral flow of the sample.

Within the portion of the sample chamber 10 where sample is imaged, the interior surfaces 16, 18 are typically, but not necessarily, substantially parallel to one another. The alignment between the base plate 12 and the upper panel 14 defines an area wherein light can be transmitted perpendicular to one panel and it will pass through that panel, the sample, and the other panel as well.

In some embodiments, at least three separators 24 (e.g., see FIGS. 1 and 2) are disposed within the sample chamber 10, in contact with both the base plate 12 and the upper panel 14. The separators 24 may be structures independent of both the base plate 12 and the upper panel 14. The separators 24 comprise an isotropic material. Examples of acceptable separators 24 include polystyrene spherical beads that are commercially available, for example, from Thermo Scientific of Fremont, Calif., U.S.A.; e.g., catalogue no. 4204A, in four micron (4 μm) diameter. Polystyrene separators formed to be essentially stress free provide desirable optical characteristics.

Some embodiments of the sample chamber 10 include one or both of a positive control area 26 (see FIGS. 3 and 4) of anisotropic crystals (or other anisotropic substances) and a negative control area 28 (e.g., one containing isotropic crystals) may be included in the light path in the focal plane of the chamber 10. Preferably, the positive and negative control structures (e.g., crystals) about the same size as the target crystals; i.e., about 0.5 microns to several microns in length. The positive control may include any type particulate or crystal that is anisotropic (i.e., birefringent), and optimally from 0.5 to two square microns in area or length. The positive control area 26 can be used to ascertain the correct functioning of the illumination, polars, focus, and visual or optical sensors. The negative control area 28 can be used to ensure that there are no anisotropic materials in the analysis area of the chamber such as anisotropic dust particles. The positive and negative control areas 26, 28 provide references that facilitate the analysis of the sample disposed within the chamber 10; e.g., the visualization of the positive control crystals or objects during cross polarization and the non-visualization of the negative control crystals or objects during cross polarization indicate proper function and use of the device. The sample chamber 10 according to these embodiments can be produced in a disposable cartridge form that includes one or both of the positive and negative anisotropic control areas 26, 28; i.e., a biologic fluid sample chamber that includes a base plate, an upper panel, at least three separators, and at least one of a positive control area and a negative control area.

Figure 1:
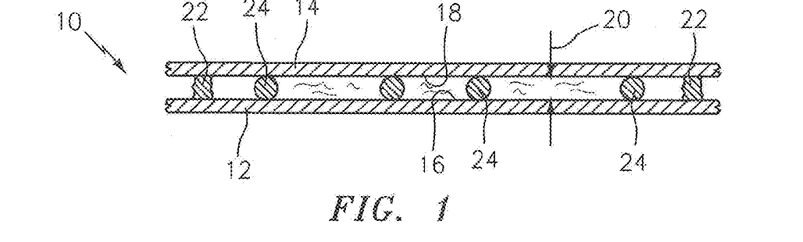
FIG. 1 is a schematic diagram of a sample chamber.
Figure 2:
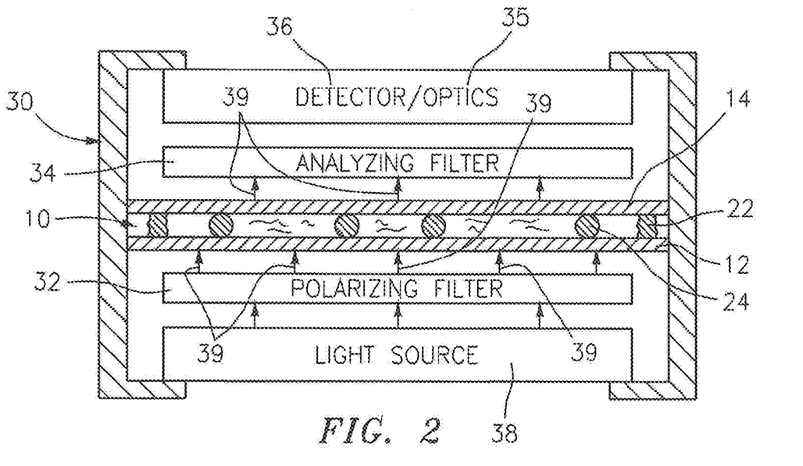
FIG. 2 is a schematic diagram of a screening device, wherein a sample chamber is disposed between a polarizing filter and an analyzing filter within a housing and arranged to have a light path from a light source, through the polarizing filter, through the sample chamber and sample disposed therein, and aligned to impinge on the analyzing filter.
Figure 3:
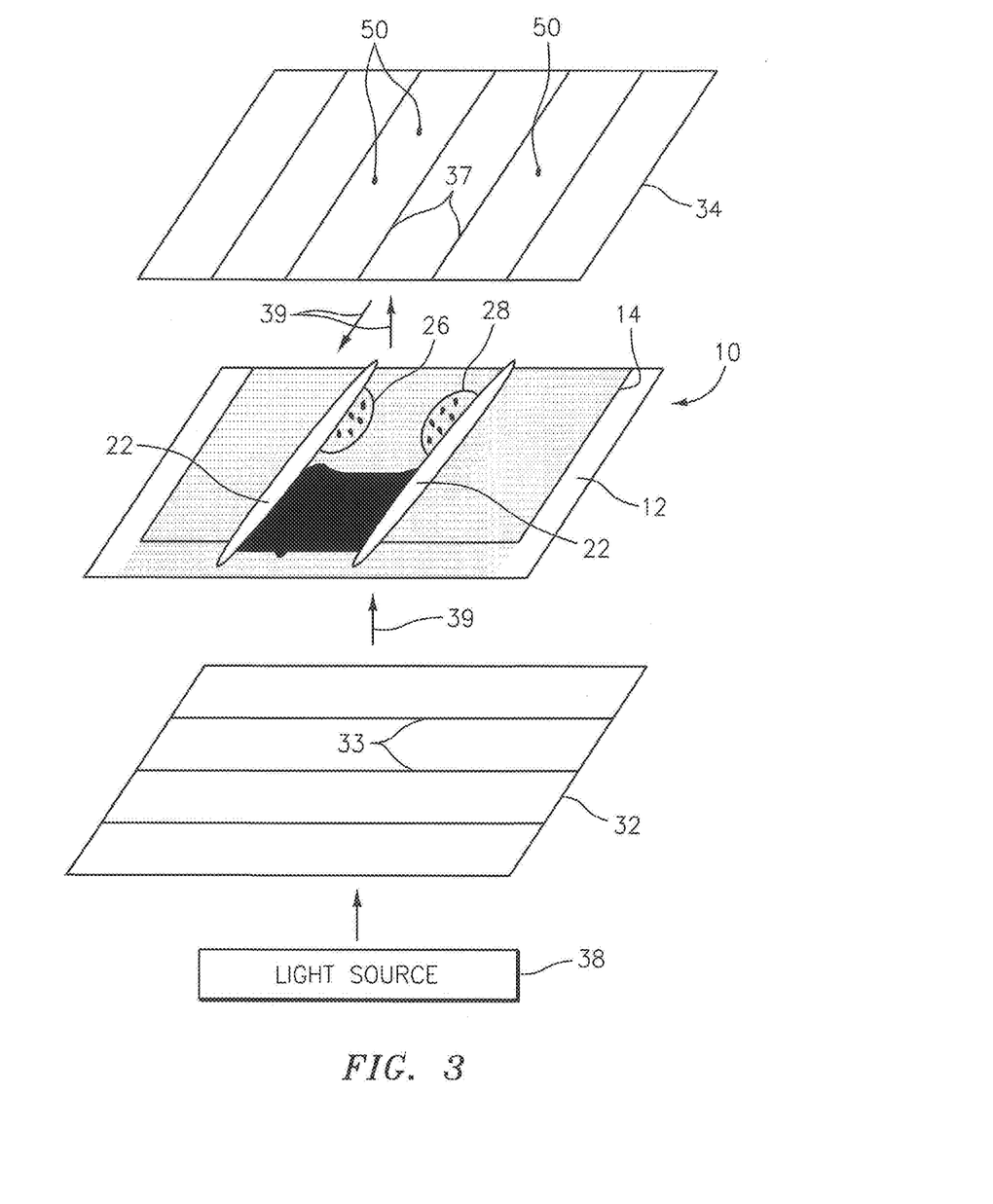
FIG. 3 is a schematic exploded view of a sample chamber, polarizing filter, analyzing filter, and light source. In this schematic depiction, the polarizing filter and the analyzing filter are disposed in a cross-polar orientation.
Figure 4:
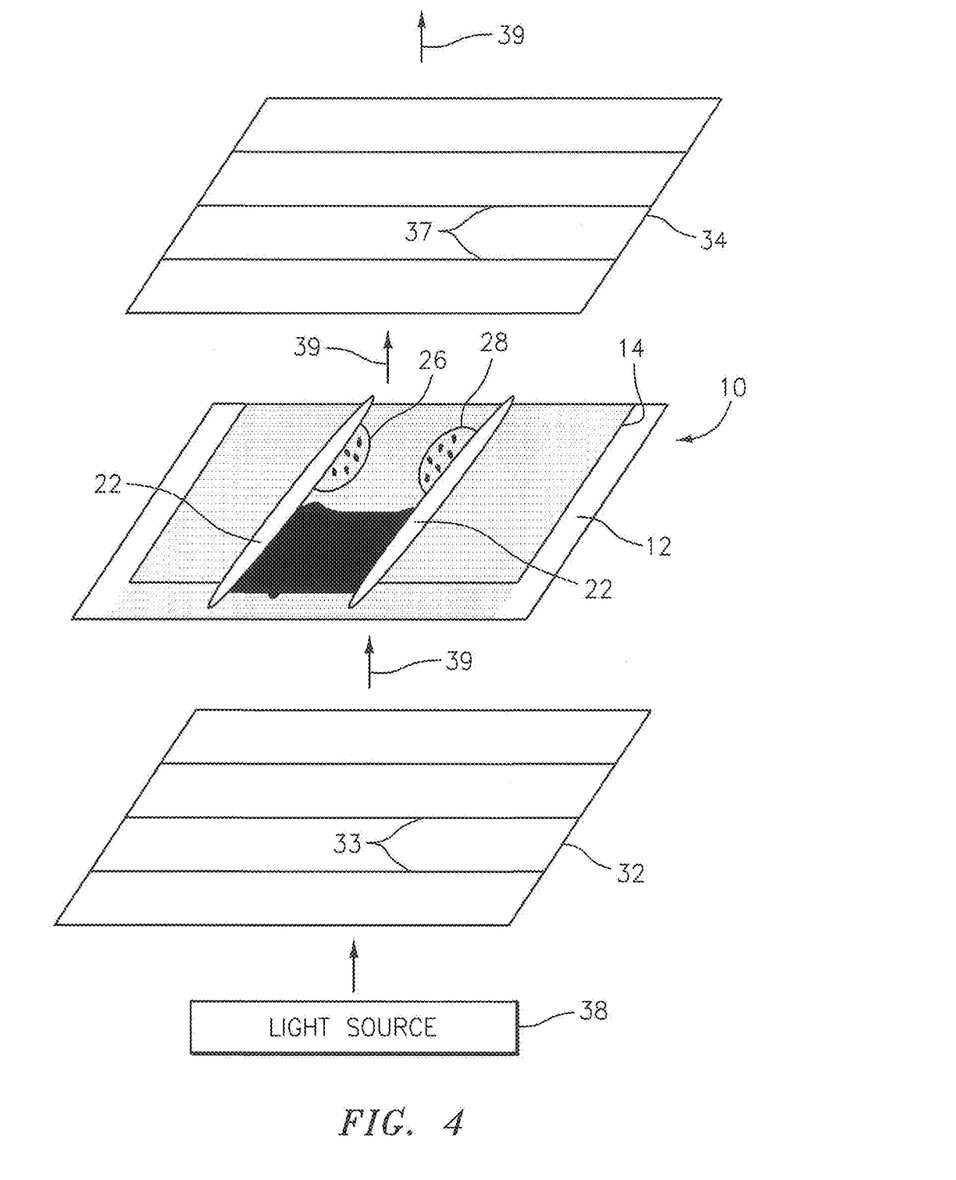
FIG. 4 is a schematic exploded view of a sample chamber, polarizing filter, analyzing filter, and light source. In this schematic depiction, the polarizing filter and the analyzing filter are disposed in a non cross-polar orientation.

The apparatus and method for screening a biologic fluid sample for anisotropic crystals can include a holding device 30 (see FIG. 2) that includes structure to hold the sample chamber 10, a polarizing filter 32 (sometimes referred to as a "polarizer"), an analyzing filter 34 (sometimes referred to as an "analyzer"), both of which filters are polarizing filters and may be referred to as "polars", and magnifying optics 35 (e.g., see FIG. 2). In some embodiments, an image detector 36 is included to capture an image of the light passing through the filters 32, 34 and sample, if any. In some embodiments, the holding device 30 may include a light source 38 (e.g., an electrically powered light source), and in other embodiments, the holding device 30 may be configured to receive light from an external light source (e.g., ambient light if sufficiently bright, or an electrically powered light source). The holding device 30 is configured to create a light path that is impervious to external light (other than light from the light source 38) and one that is internally non-reflective. Within the light path, light from the light source 38 passes through the polarizing filter 32 and becomes polarized light 39. The polarized light 39 subsequently passes through the sample chamber 10 and sample disposed therein. The polarized light 39 subsequently impinges upon the analyzing filter 34. In the screening device, the polar axis 33 of the polarizing filter 32 and the polar axis 37 analyzing filter 34 are not in agreement (sometimes referred to as "cross-polarization"; e.g., orthogonally oriented as shown in FIG. 3). As a result, the polarized light emanating from the polarizing filter 32 will not pass through the analyzing filter 34. As will be explained below, however, polarized light modified as it passes through an anisotropic crystal will pass through the analyzing filter 34, appearing as a point of light 50. An example of an acceptable magnifying optics 35 for the screening holding device is a magnifying ocular with a range of five to twenty (5-20) diopters. The chamber 10 would be placed in the focal plane of the magnifying optics.

The present invention method and apparatus for screening and analyzing a biologic fluid sample for the presence or absence of anisotropic crystals can be implemented using an analysis device 40 that includes structure for holding a sample chamber 10 (as described above) between a polarizing filter 32 and an analyzing filter 34, structure 44 for changing the polar orientation of one or both of the polars 32, 34 relative to the other, a light source 38, and a light detector 36 (e.g., an image dissector).

The structure 44 for changing the polar orientation of one or both of the polars 32, 34 relative to the other can be manually operated, or automated. For example, the structure 44 could allow the user to manually move the analyzing filter 34 relative to the polarizing filter 32 (i.e., shift the polar axis of the analyzing filter 90° relative to the polar axis of the polarizing filter) between a cross-polar orientation (e.g., see FIG. 3) and an open orientation (e.g., see FIG. 4). If the polar orientation of the polarizing filter 32 and the analyzing filter 34 are in agreement (sometimes referred to as an "open" orientation, or "non cross-polar" orientation—see FIG. 4), the polarized light will pass through the analyzing filter 34. If the polar orientation of the polarizing filter 32 and the analyzing filter 34 are not in agreement (sometimes referred to as a "closed" or "cross-polar" orientation), the polarized light will not pass through the analyzing filter 34 (see FIG. 3). As will be discussed below, in the open configuration, elements within the sample (e.g., anisotropic crystals, red blood cells, white blood cells, parasites, etc.) can be analyzed to provide useful clinical information. In an automated embodiment, the structure 44 for changing the polar orientation of one or both of the polars 32, 34 relative to the other could be automated using hardware, for example, operable to rotate one or both filters 32, 34 between a cross-polar orientation and a non cross-polar orientation. FIG. 2 schematically illustrates the polars 32, 34 in close proximity to the sample chamber. The polars 32, 34 can be alternatively placed elsewhere within the light path. The polars may be either linear or circularly polarizing filters, but polars of the linear type are preferred because they are less expensive and more efficient. The "points of light" are best visualized when the contrast is greatest, that is when the light excluded by the presence of crossed polars in the absence of anisotropic substances in its path is close to or greater than 99% of the incident light. Optimal choice of the incident light's wavelength should be chosen so that for the filters being used the greatest contrast is achieved. The efficiency of polarization of light is lower in the blue end of the visual spectrum and it is preferable to minimize blue light from the incident illumination to achieve the greatest contrast. LED's producing amber colored light (e.g., in the range of 550-575 nm) work well. A blocking filter that excludes blue light may also be employed to increase contrast. In addition, a light source 38 that provides intermittent light through the polars 32, 34 and sample chamber 10 can be used. The intermittent light (e.g., cycled at a frequency of 0.5 to 5.0 Hertz) facilitates the detection of the points of light during screening.

Figure 5:
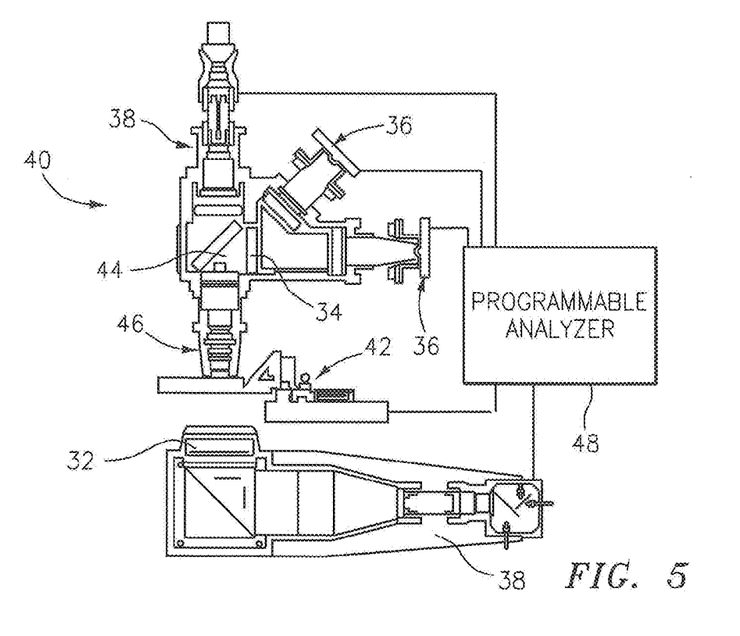
FIG. 5 is a schematic diagram of an analysis device operable to receive a sample chamber disposed between a polarizing filter and an analyzing filter, including a light source.

According to some aspects of the present invention, an automated analysis device such as that disclosed in U.S. Pat. Nos. 6,869,570; 6,866,823; or 6,929,953, each of which is hereby incorporated by reference in its entirety, could be modified pursuant to the present invention to provide an automated method and apparatus for screening and analyzing a biologic fluid sample for the presence of anisotropic crystals. FIG. 5 schematically illustrates such an analysis device 40, one that includes a cartridge holding and positioning device 42, an objective lens 46, one or more light sources 38, one or more light detectors 36 (e.g., image dissectors), and a programmable analyzer 48. One or both of the objective lens 46 and cartridge holding device 42 are movable toward and away from each other to change a relative focal position. Light transmitted through the sample, and/or fluorescing from the sample, is captured using an image dissector 36, and a signal representative of the captured light is sent to the programmable analyzer 48, where it is processed into an image and analyzed. The programmable analyzer 48 includes a central processing unit (CPU) and is in communication with the cartridge holding and manipulating device 42, the light sources 38, and the image dissectors 36. The programmable analyzer 48 is adapted (e.g., programmed) to selectively perform the functions necessary to perform the present method; e.g., to receive the signals and selectively perform the functions necessary to operate the cartridge holding and manipulating device 42, the light sources 38, the light detectors 36, and the structure 44 for changing the polar orientation of one or both of the polars 32, 34. It should be noted that the functionality of programmable analyzer 48 may be implemented using hardware, software, firmware, or a combination thereof. A person skilled in the art would be able to program the analyzer 48 to perform the functionality described herein without undue experimentation. The programmable analyzer 48 is further adapted to process the image signals to identify the points of light 50 present, if any, when the sample is interrogated with the polars 32, 34 disposed in a cross-polarization configuration. If points of light 50 are identified, the programmable analyzer 48 is adapted to cause the polar orientation of the filters 32, 34 to change into an "open" configuration (or to remove the polars 32, 34 from the light path entirely) to allow the sample to be analyzed via light transmitted through the sample and/or fluorescent light emanating from the sample. The illumination and examination utilizing fluorescence may also, if performed with an epi-illuminating source, be performed with the polars closed, but it is more efficiently performed with the polars open or absent from the light path so that simultaneous analysis of transmitted light may be accomplished.

An example of an acceptable image dissector 36 is a charge couple device (CCD) type image sensor that converts light passing through (or from) the sample into an electronic data format image. Complementary metal oxide semiconductors ("CMOS") type image sensors are another example of an image sensor that can be used. The signals from the image dissector provide information for each pixel (or other area unit) of the image, which information includes, or can be derived to include, intensity, wavelength, and optical density. Intensity values are assigned an arbitrary scale of, for example, 0 units to 4095 units ("IVUs"). Optical density ("OD") is a measure of the amount of light absorbed relative to the amount of light transmitted through a medium; e.g., the higher the "OD" value, the greater the amount of light absorbed during transmission.

In the operation of the invention, a biological fluid sample (e.g., undiluted whole blood) is disposed to quiescently reside within the sample chamber 10. The term "quiescent" is used to describe that the sample is deposited within the chamber for analysis, and the sample is not purposefully moved relative to the chamber during the analysis; i.e., the sample resides quiescently within the chamber. To the extent that motion is present within the blood sample, it will predominantly be that due to Brownian motion of the blood sample's formed constituents, which motion is not disabling of the use of the device of this invention. The sample chamber height (e.g., typically between 4 and fifteen microns—4-15µ) is such that the sample contacts the interior surfaces 16, 18 of both the upper panel 14 and the base plate 12, and is thin enough so that constituents (e.g., red blood cells) within the sample other than anisotropic crystals do not substantially obscure the transmission of light through anisotropic crystals that may be present within the sample chamber 10.

Figure 6:
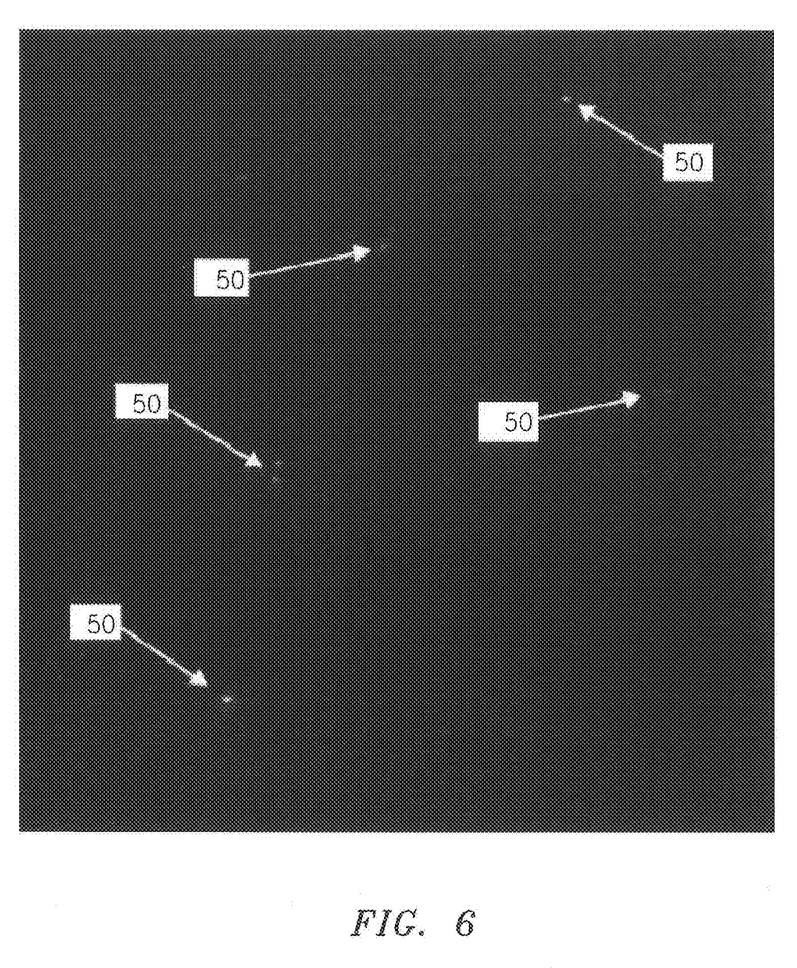
FIG. 6 is an image of a sample taken with the polarizing filter and the analyzing filter in a cross-polarization orientation, which image includes a plurality of points of light, each associated with an anisotropic crystal.

In the case of a method and apparatus for screening a biological fluid sample for the presence of anisotropic crystals, the sample chamber 10 containing a biologic fluid sample may be inserted into the holder 30 between the polarizing filter 32 and the analyzing filter 34 (also a polarizing filter). The polars 32, 34 are oriented in a cross-polar configuration such that light emanating from the light source 38, and becoming polarized through the polarizing filter 32, will pass through the sample chamber 10 but will be blocked by the analyzing filter 34, and therefore will not pass through the analyzing filter 34. In the event anisotropic crystals are present within the biological fluid sample (e.g., hemozoin crystals present within a blood sample as a result of malarial parasites), polarized light passing through the anisotropic crystals will change polarization into a form that at least a portion of which will be able to pass through the analyzing filter 34. As a result, an image is produced that includes a dark background (created by the blocked polarized light) with some number of points of light 50 created by the light altered during passage through the anisotropic crystals. The image shown in FIG. 6 illustrates a number of points of light 50 present within the image, indicating the presence of anisotropic crystals within the sample. The points of light 50 establish the presence of anisotropic crystals within the sample. As indicated above, the sample chamber 10 may include one or both of a positive control area 26 of anisotropic crystals and a negative control area 28 without anisotropic crystals, which control areas are disposed within the sample chamber so they are in (or can be moved in) the light path in the focal plane of the chamber 10. The positive and negative control areas 26, 28 can be evaluated to determine the screening device is working accurately, and the identified points of light 50 within the sample can be compared against the positive and negative control areas 26, 28 to facilitate the analysis of the sample disposed within the chamber 10.

In the case of a device method and apparatus for screening and analyzing a biologic fluid sample for the presence or absence of anisotropic crystals, the sample chamber 10 containing a biologic fluid sample is inserted between the polarizing filter 32 and the analyzing filter 34. As will be explained below, it is useful to mix one or more non-anisotropic colorants (e.g., acridine orange) with the sample disposed within the chamber 10. To screen the sample for the presence of anisotropic crystals, the polar filters 32, 34 are oriented in a cross-polar configuration such that polarized light emanating from the polarizing filter 32 will pass through the sample chamber 10 but will be blocked by the analyzing filter 34, and therefore will not pass through the analyzing filter 34. Polarized light modified as it passes through anisotropic crystals within the sample will change polarization an amount that allows at least a portion of the modified light to pass through the analyzing filter 34 and appear as a point of light 50 in the "screening" image (e.g., see FIG. 6). The screening image will include a dark background (created by the blocked polarized light), and if there is "n" number of anisotropic crystals present, will also include "n" points of light created by the light altered during passage through the anisotropic crystals, where "n" in an integer equal to or greater than one (see FIG. 6). Here again, the sample chamber 10 may include a positive and/or a negative control area 26, 28 to facilitate the analysis. The examination of the image to detect points of light 50 indicative of an anisotropic crystal can be done at a first magnification (e.g., 20×) to facilitate the examination of areas of the relatively thin sample layer.

Figure 7:
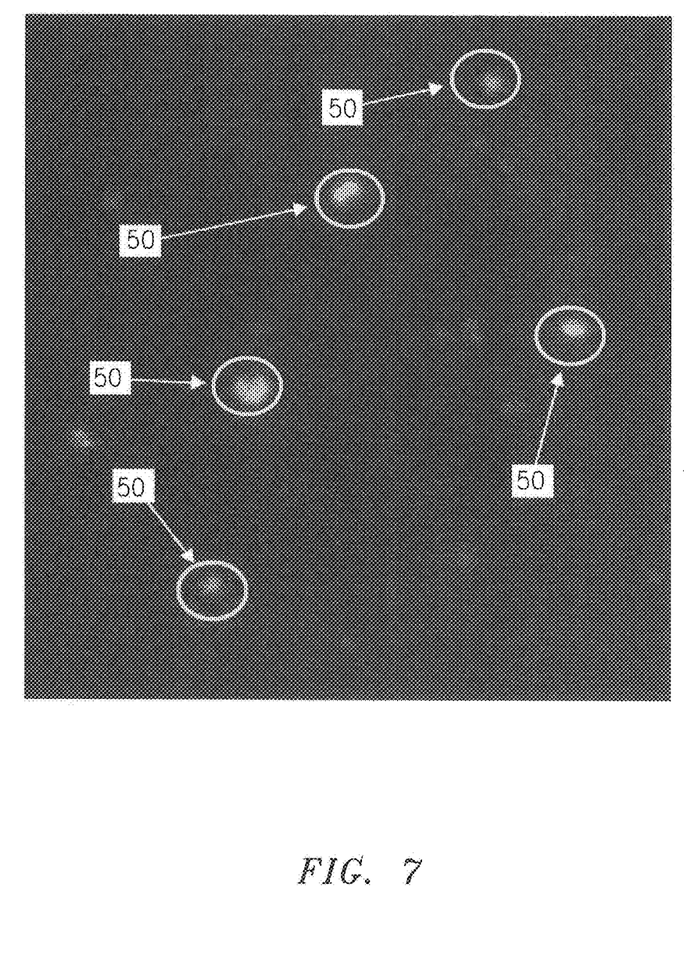
FIG. 7 is an image of the sample portion shown in the FIG. 4 image, taken with the polarizing filter and the analyzing filter in a non cross-polarization orientation, illustrating fluorescent images portions associated with each point of light shown in FIG. 6.
Figure 8:
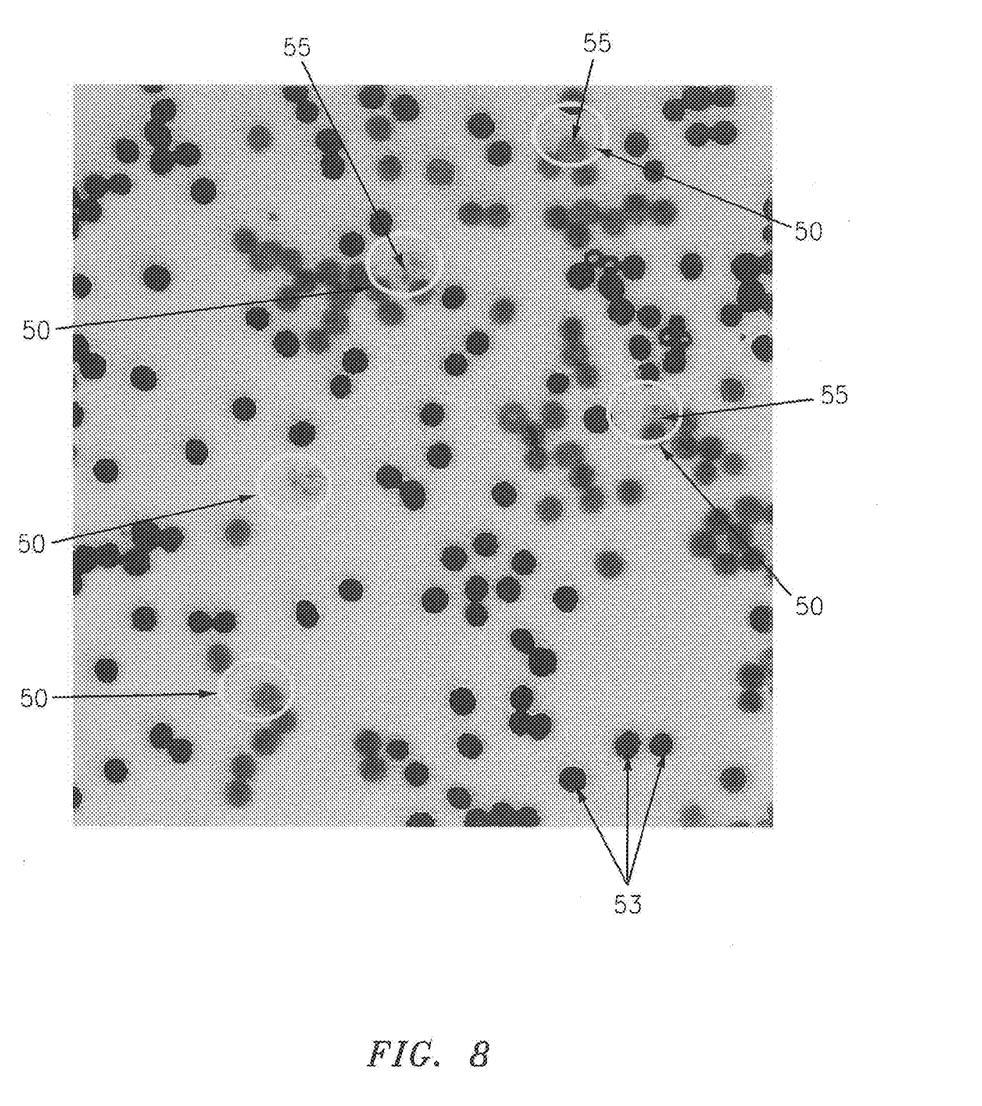
FIG. 8 is a transmittance image of the sample portion shown in FIGS. 6 and 7, with the polarizing filter and the analyzing filter in an open configuration, so as to permit the transmission measurement/observation.

In the event the screening reveals the presence of one or more anisotropic crystals, the relative orientation of the filters 32, 34 can be changed to a non cross-polar configuration that allows the transmission of light through both the filters 32, 34; e.g., transmission from the light source and/or fluorescent light emanating from the sample passing through the analyzing filter 34. The detected points of light can then be analyzed for additional information; e.g., size and shape of associated crystals. The analysis can be done in real time or can be based on an image created with the filters 32, 34 in a non cross-polar orientation. When a point of light 50 is detected the technician may switch to a higher magnification (e.g., a 50× or 100× oil immersion) and examine the source of the light with the specimen centered on that source. The points of light 50 may be associated with crystals associated with malarial parasites located within a red blood cell, or may be crystals independent of a cellular host. Colorants may be used to determine the presence of a cell; e.g., red blood cells, granulocytes, monocytes, etc. For example, acridine orange added to a blood sample can be used to confirm the presence of the malarial parasite within a red blood cell (as can be seen in FIG. 7 via fluorescence), and the morphology of the parasite can be used to speciate the malarial parasite. For example, acridine orange will interact with RNA or DNA within a malarial parasite and will fluoresce when exposed to excitation light (see FIG. 7). Good results have been achieved by including an amount of acridine orange in the sample chamber that is sufficient to yield a final concentration of from 50 to 150 nanograms per micro liter of blood. The volume of the chamber will depend upon the height and area, and will, assuming a four micron (4μ) chamber height and a filled area of one square cm, be about 0.4 microliters (0.4 μl). Once a parasite is located, it can be further inspected to determine the specific type of parasite via its morphology preferably by fluorescent imaging utilizing the morphology of the parasite accentuated by the acridine orange staining of the parasite in the non-fluorescent red blood cell as shown in FIG. 7. FIG. 8 is a transmittance image of the sample shown in FIGS. 6 and 7, now imaged in a manner that permits the morphology of the parasites to be determined and the parasites speciated. As a result, treatment can be focused on that particular species of parasite. The analysis of the sample is not limited to the above example, but in fact can be used with any analysis that is useful once the presence of anisotropic crystals is determined within the sample.

In an alternative embodiment, the presence of hemozoin crystals inside red blood cells may be determined by evaluating the sample image for red blood cells having one or more small, concentrated regions of low transmission at least partially surrounded by regions of higher transmission and/or a fluorescent signature associated with a hemozoin producing parasite. As indicated above, the sample may be imaged and analyzed according to the embodiments of the present invention using an automated analysis device such as that disclosed in U.S. Pat. Nos. 6,869,570; 6,866,823; or 6,929,953, adapted to perform the methodology described herein. The low transmission regions at least partially surrounded by the high transmission regions result from localization of hemozoin byproduct from hemoglobin digestion caused by the parasite; e.g., a malarial parasite. The terms "lower transmission" and "higher transmission" are used to describe a relative difference in transmittance within a red blood cell (RBC) image when the sample is subjected to transmission light at a wavelength of about 410-420 nm (preferably 413 nm). In the transmittance image shown in FIG. 8, for example, unaffected RBCs 53 appear as relatively dark, uniformly-colored circles, and affected RBCs appear as having areas of low and high transmission (e.g., localized dark colored low transmittance regions surrounded by light colored higher transmittance areas). The darkness of the low transmission regions is a function of the hemozoin within each RBC absorbing light transmitted through the sample at the aforesaid wavelength (s). The RBCs appear substantially uniformly circular in FIG. 8 because they have been subjected to an isovolumetric sphering agent. Hence, the presence of hemozoin crystals within RBCs within a sample can be determined by quantitatively evaluating the RBCs within the sample and determining the presence of RBCs with localized areas of low transmission at least partially surrounded by areas of higher transmission. The evaluation may include comparing the hemoglobin content and/or concentration of RBCs identified as having hemozoin crystals versus the hemoglobin content of RBCs within the sample that do not have crystals. The determination of the hemoglobin content and/or concentration within a RBC may be performed using a methodology such as, but not limited to, that disclosed in U.S. patent application Ser. No. 13/051,705, "Method and Apparatus for Determining at Least One Hemoglobin Related Parameter of a Whole Blood Sample", which application is hereby incorporated by reference in its entirety. In this embodiment, a sample chamber made of an isotropic material can be used, but is not required. In addition, in this embodiment the presence of hemozoin crystals can be determined without the use of polarized filters (e.g., polarizing filter 32, analyzing filter 34). Hemozoin crystals inside a RBC are produced by a parasite (e.g., a malarial parasite) as a waste product. The parasites contain DNA and RNA that, when stained with a nucleic acid stain such as acridine orange, can produce a fluorescent "signature" that is distinguishably associated with that particular type of parasite. The image analysis of this embodiment can be performed by an automated analysis device such as those disclosed in U.S. Pat. Nos. 6,869,570; 6,866,823; or 6,929,953, modified pursuant to the present invention. The present invention is not limited to using these analysis devices, however. The combination of the present method using polar filters to identify hemozoin crystals and the alternative embodiments that identifies RBCs containing hemozoin (via transmission alone, or with fluorescent signature) can be an effective tool for verifying the presence of hemozoin crystals, and thereby increasing the accuracy of the determination. For example, dust particles or other debris on or in a sample chamber 10 may on occasion appear within an image as a point of light 50. The alternative embodiment identifying RBCs containing hemozoin crystals via transmission can be used to confirm the presence (or absence) of the crystals since a RBC that happens to align with the aforesaid dust particle will not also have a depleted amount of hemoglobin.

In some embodiments, the entire sample layer disposed within the sample chamber 10 may be electronically imaged at a lower magnification, and portions of the image of the entire sample where points of light 50 are identified can be mapped and imaged at a higher level of magnification. The image portions associated with the points of light can be examined in detail via the device used to image the sample, or the electronic image (or image portions) can be transferred telemetrically to a remote site where expertise is present. The size of the crystal(s) and the percentage of cells having detectable crystals within the sample may be determined.

Figure 9:
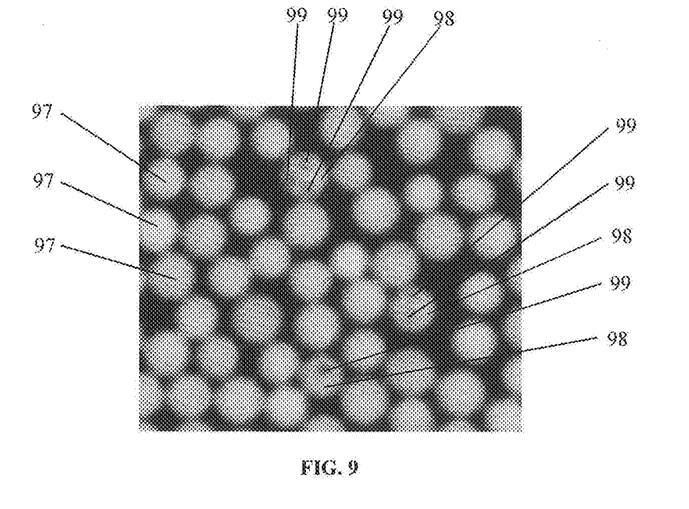
FIG. 9 is an image of optical density of a blood sample illustrating red blood cells (RBCs) with displaced regions of hemoglobin.
Figure 10:
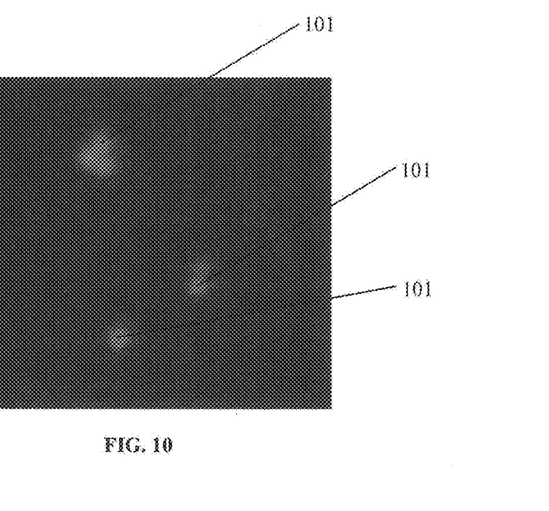
FIG. 10 is an epi-illumination image of the sample shown in FIG. 9 illustrating fluorescent illumination at the displaced regions.

Aspects of the present invention can also be used to detect the presence of intraerythrocytic organisms (e.g., malarial parasites, babesia parasites, etc.) within sphered RBCs by detecting localized regions 99 of decreased hemoglobin content and/or concentration within one or more RBCs due to the displacement of hemoglobin within those RBCs by the intraerythrocytic organism located within the infected RBC, which organism may or may not contain hemozoin. The hemoglobin content/concentration within a "decreased" region 99 is, of course, relative to the hemoglobin content/concentration in the remaining region 98 of the RBC which is not occupied by the parasite. The hemoglobin content and/or concentration is preferably, but not necessarily, measured in each RBC because hemoglobin content/concentration can vary on an individual RBC basis (e.g., a first RBC may have a hemoglobin concentration value of "X", and a second RBC may have a hemoglobin concentration of "Y", where X≠Y). Measuring hemoglobin content and/or concentration on a cell by cell basis permits the determination of specific values for individual RBCs. As indicated above, the determination of the hemoglobin content and/or concentration within a red blood cell may be performed using a methodology such as, but not limited to, that disclosed in U.S. patent application Ser. No. 13/051,705, "Method and Apparatus for Determining at Least One Hemoglobin Related Parameter of a Whole Blood Sample", which application is incorporated by reference above. The ability to detect such localized "decreased hemoglobin" regions within a RBC is facilitated if the RBC is sphered (e.g., using a isovolumetric sphering agent), and/or the sample is imaged in a mono layer as can be done in the analysis chambers described above (also as described in U.S. Patent Publication No. 2007/0243117 and U.S. patent application Ser. No. 12/971,860). The present invention is not, however, limited to methodologies that use sphered RBCs and/or monolayers, however. The imaging may be accomplished, for example, via trans-illumination at a wavelength of about 410 to 420 nm, although any wavelength well absorbed by hemoglobin may be used. The displacement of hemoglobin by the organism (i.e., the local regions 99 of decreased hemoglobin content/concentration) can be seen in FIG. 9 as a region of decreased optical density (i.e., a relatively higher transmission region which appears darker in the transmission image) occupying about 5% to 95% of the interior of the RBC. The exact size of the region of decreased hemoglobin content/concentration can vary due to factors such as the stage of the parasite. For example, the volume of a parasite (e.g., a malarial parasite) within a RBC typically increases with stage, and consequently assumes a growing percentage of the volume of the RBC. The presence of a parasitic organism (e.g., malaria in the example shown in FIGS. 9 and 10) may be confirmed by the image shown in FIG. 10 which was taken with epi-illumination at 470 nm with an appropriate fluorescent dye added to the sample. The fluorescently illuminated organisms 101 are located in the exact positions of the displaced hemoglobin. The ability of this aspect of the present method to determine the presence of a intraerythrocytic organism in this embodiment of the invention utilizes the displacement of the hemoglobin within the RBC, as opposed to the decreased content or concentration of hemoglobin within the RBC caused by the activity of the organism. The sphering of the RBC, by any means known to effect isovolumetric sphering, is done to facilitate the detection of localized decrements in optical density. The optical density of RBCs that are not infected by an intraerythrocytic organism (i.e., non-infected RBCs 97) appears homogeneous and without any discernible differences in optical density.

Figure 11:
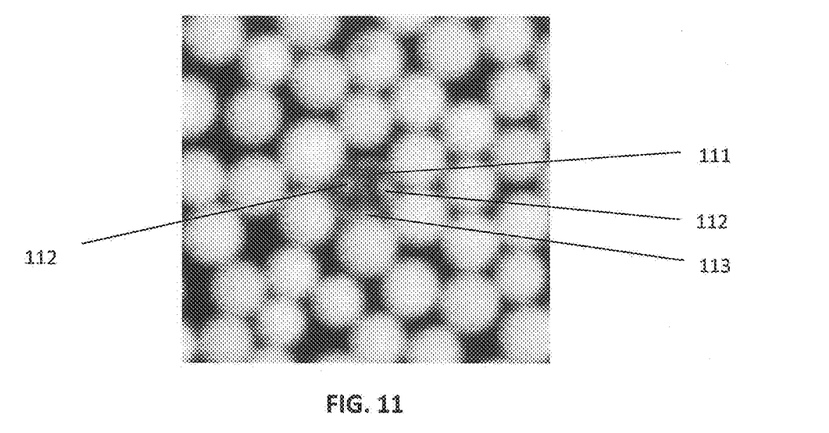
FIG. 11 is an image of optical density of a blood sample illustrating an infected RBC with displaced regions of hemoglobin and relatively increased optical density due to hemozoin.

Imaging of hemozoin crystals produced by intracellular parasites may be accomplished with trans-illumination at a wavelength of about 410 to 420 nm, although any wavelength absorbed well by hemozoin may be used. FIG. 11 shows an infected RBC with two intraerythrocytic malaria parasites imaged with 413 nm trans-illumination. A localized region of decreased optical density 111 is caused by displacement of hemoglobin as in the same manner as FIG. 9 as previously described. A region 112 of increased optical density (relative to the decreased optical density region 111) is caused by an accumulation of hemozoin, which absorbs relatively more 413 nm trans-illumination light than the malaria parasite that produces the hemozoin. The region 113 of the cell that is not occupied by the malaria parasite or hemozoin exhibits an optical density that is greater than the optical density of the region 111 occupied by the parasite. The optical density of the RBC region 113 (not occupied by parasite or hemozoin) is approximately equal in magnitude with the optical density of the region 112 occupied by the hemozoin. Hematophagus parasites consume the hemoglobin of RBCs and therefore the region 113 may or may not exhibit reduced optical density relative to non-infected RBCs. Detectible hemozoin is not typically produced by hematophagus parasites (e.g. malaria) until more advanced stages have developed and other non-hematophagus intraerythrocytic parasites do not ever produce hemozoin. The relative increased optical density of hemozoin is therefore not suitable as an exclusive screening method for intraerythrocytic parasites but is useful as a confirmatory analysis of hematophagus parasite infection and as a method for differentiation of hematophagus parasites from non-hematophagus parasites.

Figure 12:
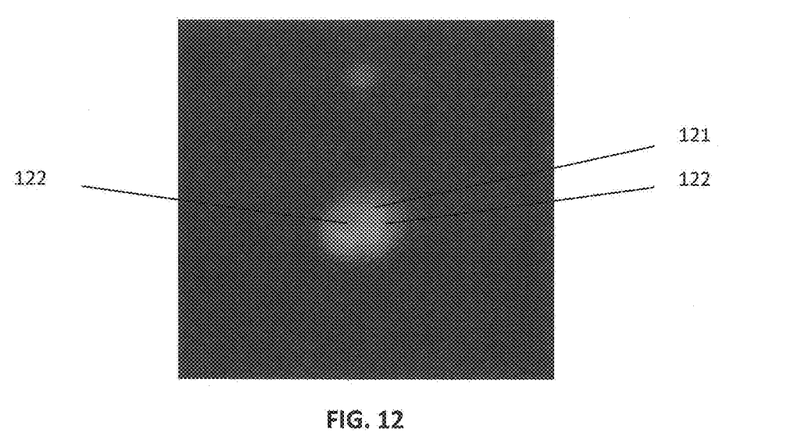
FIG. 12 is an epi-illumination image of the sample shown in FIG. 11 illustrating fluorescent illumination at the regions of low optical density and a lack of fluorescent illumination at the regions of relatively increased optical density.

The fluorescence of a typical late-stage malaria parasite by epi-illumination at 470 nm of the sample in FIG. 11 is shown in FIG. 12. The fluorescent illumination of late-stage parasites 121 is typically increased relative to the fluorescent illumination of early-stage parasites 101. The regions in which the accumulated hemozoin 112 reside (as indicated by the relative increased optical density of FIG. 11) exhibit a decreased fluorescent illumination 122 relative to the fluorescent illumination of the malaria parasite 121. This is due to the volume displaced by the hemazoin within the parasite, and the fact that hemozoin does not contain DNA or RNA and therefore a supravital stain, e.g. acridine orange, will not bind to the crystalline structure to fluorescently illuminate.

Figure 13:
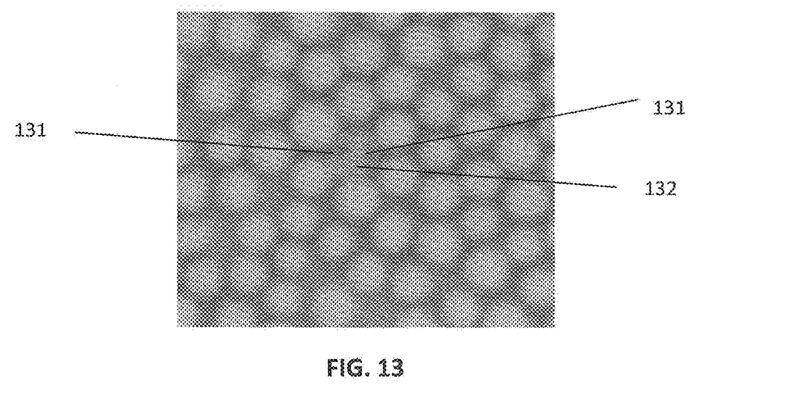
FIG. 13 is an image of optical density of the blood sample in FIGS. 11 and 12 illustrating an infected RBC with two regions of decreased optical density relative to the remainder of the cell.

Using trans-illumination at 660 nm, the infected RBC of FIG. 13 exhibits two regions of decreased optical density 131 in which the hemozoin 112 resides, relative to the optical density of the region of the RBC in which hemozoin does not reside 132. The decreased optical density occupies about 5% to 95% of the total interior of the RBC, depending on the number of hemozoin deposits. The number of hemozoin deposits is often directly correlated with the number of intraerythrocytic parasites. Imaging may be accomplished via trans-illumination at a wavelength of about 650 to 670 nm, although any wavelength that differentiates hemozoin from the other regions of the cell may be used.

The combination of techniques as discussed and shown in FIGS. 11-13 can be used to differentiate early and late-stage intraerythrocytic parasites, as well as to differentiate hematophagus and non-hematophagus intraerythrocytic parasites. The presence of hemozoin crystals may likewise be determined using these criteria in addition to or separate from the previously described cross-polarization methods.

Certain medical conditions, e.g. hypersplenia or asplenia, contribute to an increased occurrence of intracellular inclusions within RBCs known as Howell-Jolly bodies. Howell-Jolly bodies are dense basophilic nuclear remnants that are normally filtered out by the spleen but remain within RBCs in diminished or absent splenic function. Using aspects of the present method described herein, Howell-Jolly bodies appear somewhat similar in appearance to intraerythrocytic parasites but several methods exist for differentiation. Howell-Jolly bodies are theoretically capable of displacing hemoglobin similar to intracellular parasites, but unlike intraerythrocytic parasites, the localized decrement of hemoglobin due to decreased absorbance at 413 nm is not perceptible. Howell-Jolly bodies may also be differentiated from intracellular parasites on the basis of their fluorescent intensity. A supravital stain, e.g. acridine orange, binds to the DNA of Howell-Jolly bodies and exhibits green fluorescence that is typically two times greater in intensity than the green fluorescence of intracellular parasites, where the fluorescent intensity may be defined as a pixel value measurement from a 12-bit CCD camera with quantized levels ranging from 0 to 4096. Another distinguishing feature of Howell-Jolly bodies is the pixel region of green fluorescent illumination, which is typically much smaller than early-stage intraerythrocytic parasites, e.g. a malaria ring-stage trophozoite. Later stage intraerythrocytic parasites (e.g. a malaria late-stage trophozoite) exhibit a significantly larger green fluorescence pixel area relative to Howell-Jolly bodies by as much as ten times. Finally, intraerythrocytic parasites are capable of occupying RBCs with more than one parasite either through asexual reproduction in the RBC or by invasion of the RBC with more than one parasite. Typically, only one Howell-Jolly body occupies an RBC at any given time.

The benefits of the invention include: a) lower cost/test for screening; b) greatly lower capital cost for screening; c) immediate availability of result at point of care; d) ease of use by untrained observer; e) automatic calculation of parasitemia magnitude; f) quality control can performed at the point of use; g) immediate epidemiological information immediately available so that control measures may be employed (i.e., mosquito or vector control); h) immediate medical treatment may be given; and i) market expansion for the manufacturer due to lower regulatory burden for the physicians.

What is claimed is:

1. A method of determining the presence of an intraerythrocytic organism within a sample of liquid whole blood, comprising the steps of:
   providing an apparatus that includes at least one light source, at least one light detector, and a programmable analyzer;
   creating an image of the sample quiescently residing within a sample chamber using the light source and light detector, which imaging includes trans-illuminating the sample with light from the light source at one or more wavelengths absorbed by hemoglobin;
   using the analyzer to evaluate the image for the presence of at least one red blood cell within the image containing at least one first region of decreased hemoglobin content and/or hemoglobin concentration within the red blood cell, which red blood cell has an otherwise homogenous distribution of hemoglobin; and
   using the analyzer to determine the presence of an intraerythrocytic organism within the sample based on the image.

2. The method of claim 1, wherein the sample is trans-illuminated by light in the range of about 410-420 nm.

3. The method of claim 1, wherein the evaluating step includes using optical density to identify the first region of decreased hemoglobin content and/or hemoglobin concentration within the red blood cell.

4. The method of claim 3, wherein the evaluating step includes identifying a second region within the red blood cell having an optical density value different than an optical density value of the first region.

5. The method of claim 3, wherein the evaluating step includes determining a second region within the identified red blood cell having the homogenous distribution of hemoglobin.

6. The method of claim 5, wherein the evaluating step includes determining a third region contiguous with the first region, which third region has an optical density value greater than that of the first region.

7. The method of claim 6, wherein the optical density of the third region is substantially equal to that of the second region.

8. The method of claim 1, wherein the evaluating step further includes identifying a region surrounded by the first region, which region has an optical density value greater than that of the first region.

9. The method of claim 1, wherein if an intraerythrocytic organism is determined to be present within the sample, the method further comprising the step of determining if the organism is hematophagus or non-hematophagus.

10. The method of claim 1, wherein the evaluating and determining steps are performed by a processor adapted to perform the aforesaid steps.

11. The method of claim 1, further comprising the steps of:
    adding a fluorescent dye to the sample;
    epi-illuminating one or more of the identified red blood cells at one or more first wavelengths of light operable to cause dye residing within an intraerythrocytic organism to fluorescently emit light at one or more second wavelengths of light; and
    analyzing the image of the one or more identified red blood cells for the second wavelengths of emitted light.

12. The method of claim 11, wherein the analyzing step further includes the steps of:
    determining intensity values of the light fluorescently emitted from the identified red blood cells; and
    identifying a presence of hemazoin using relative differences in the determined intensity values of the light fluorescently emitted from the identified red blood cells.

13. The method of claim 11, wherein the analyzing step further includes the steps of:
    determining intensity values of the light fluorescently emitted from the identified red blood cells; and
    identifying a type of the intraerythrocytic organism using relative differences in the determined intensity values of the light fluorescently emitted from the identified red blood cells.

14. The method of claim 11, wherein the analyzing step further includes the steps of:
   determining intensity values of the light fluorescently emitted from the identified red blood cells; and
   determining the presence of one of more Howell-Jolly bodies within the identified red blood cells using the determined intensity values of the light fluorescently emitted from the identified red blood cells.

* * * * *